(12) United States Patent
Murphy et al.

(10) Patent No.: US 6,294,915 B1
(45) Date of Patent: Sep. 25, 2001

(54) INTERIOR ALIGNMENT LIGHT FOR OPEN MAGNET MRI

(75) Inventors: Lawrence E. Murphy, Milwaukee; Bobby Glenn Keen, New Berlin, both of WI (US)

(73) Assignee: General Electric Company, Milwaukee, WI (US)

( * ) Notice: Subject to any disclaimer, the term of this patent is extended or adjusted under 35 U.S.C. 154(b) by 0 days.

(21) Appl. No.: 09/274,374

(22) Filed: Mar. 23, 1999

(51) Int. Cl.$^7$ ........................................ G01V 3/00
(52) U.S. Cl. .......................... 324/318; 324/319
(58) Field of Search ...................... 324/318, 309, 324/307, 319, 320; 378/20, 17; 356/153; 600/407

(56) References Cited

U.S. PATENT DOCUMENTS

| 4,538,289 |   | 8/1985 | Scheibengraber | 378/20 |
| 4,841,967 | * | 6/1989 | Chang et al. | 606/130 |
| 5,769,787 | * | 6/1998 | Limelson | 600/407 |
| 6,049,208 | * | 4/2000 | Takekoshi et al. | 324/319 |

FOREIGN PATENT DOCUMENTS

| 44 40 225 | 3/1996 | (DE) . |
| 0 373 000 | 6/1990 | (EP) . |
| 0 577 001 | 1/1994 | (EP) . |

\* cited by examiner

*Primary Examiner*—Jay Patidar
*Assistant Examiner*—Tiffany A. Fetzner
(74) *Attorney, Agent, or Firm*—Timothy J. Ziolkowski; Christian G. Cabou; Phyllis Y. Price

(57) ABSTRACT

A patient alignment device is disclosed for use in open magnet MRI having a movable patient table to move a patient within the open magnet MRI in order to position a desired patient scan area accurately within the field-of-view (FOV) of the open magnet MRI. A first alignment light is placed on the outer periphery of the upper magnetic structure of the open MRI to emit a light beam in longitudinal alignment with a center point of the FOV. A second alignment light is positioned to emit a second light beam downwardly from the upper magnetic structure to indicate an interior reference point of the FOV. The second alignment light is then used to reposition a patient within the open magnet MRI without having to withdraw the patient from the open magnet MRI.

24 Claims, 3 Drawing Sheets

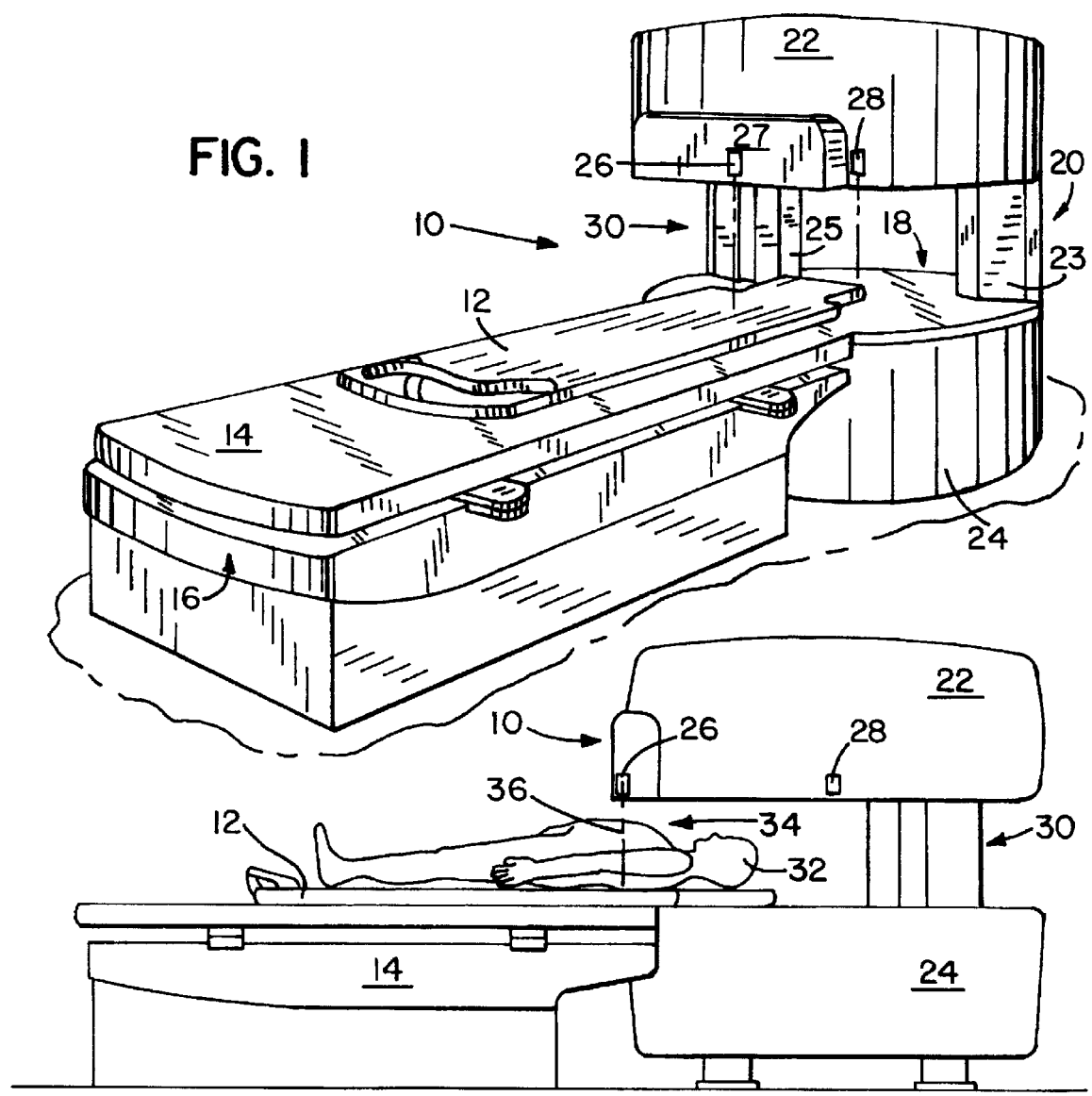
FIG. 1
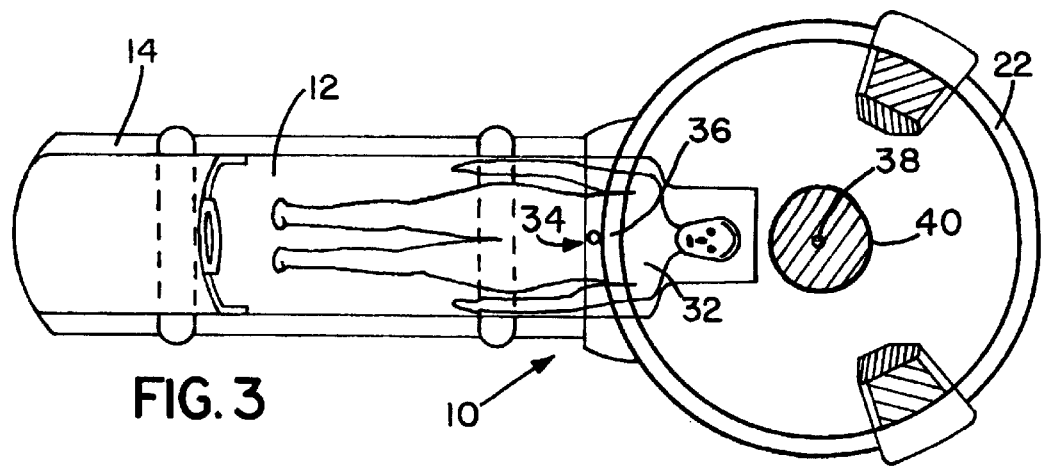
FIG. 2
FIG. 3

INTERIOR ALIGNMENT LIGHT FOR OPEN MAGNET MRI

BACKGROUND OF THE INVENTION

The present invention relates generally to magnetic resonance imaging (MRI), and more particularly to a system and method for aligning a patient in an open magnet MRI.

In open magnet magnetic resonance imaging (MRI), it is critical to position a patient such that the specific area to be scanned is positioned centrally within the field-of-view (FOV) of the MRI device. This is so because such open magnet MRI devices are constructed with relatively low magnetic induction permanent magnets. Typically the FOV imaging area is no more than approximately 40 cm. In order to acquire a quality image from a limited FOV, it is desirable to have the desired patient scan area centrally located within the FOV.

In order to locate the desired scan area within the FOV, prior art devices have used an alignment light on the outer periphery of the MRI housing to align a patient before entering the MRI. In operation, the MRI operator turns on the alignment light and manually positions the patient such that the light is directed to the area that the MRI operator desires to acquire an MRI scan. An automated moveable patient table then automatically moves the patient into the open magnet MRI a given distance as defined by the position of the exterior alignment light to the center of the FOV. Once an initial scan is taken, and the MRI operator determines that the patient is not properly positioned from reviewing the initial scan, the patient is withdrawn from the MRI device and realigned using the exterior light and the MRI image as reference points.

Such realignment techniques are time consuming and are an annoyance to patients. Therefore, it would be desirable to have an interior alignment light to indicate the center of the FOV without having to withdraw the patient.

SUMMARY OF THE INVENTION

The present invention provides a method for repositioning a patient within an open magnet MRI and an interior positioning light for use in open magnet MRI devices that overcomes the aforementioned problems.

A patient positioning device is disclosed for use in open magnet MRI having a moveable patient table to move a patient within the open magnet MRI in order to position a desired patient scan area accurately within the FOV of the open magnet MRI. A first alignment light is located on the outer periphery of the upper magnetic structure of the open MRI to emit a light beam in longitudinal alignment with a center point of the FOV. A second alignment light is positioned to emit a second light beam downwardly from the upper magnetic structure to indicate an interior reference point of the FOV. The second alignment light is then used to reposition a patient within the open magnet MRI without having to withdraw the patient from the open magnet MRI.

In accordance with one aspect of the invention, a patient positioning device for use in medical imaging of patients has a medical imaging housing accepting therein a moveable table for placement thereon of a patient. An interior alignment light emitting an interior light beam toward a patient on the moveable table within the housing is provided to align a desired scan area of the patient within a scanning region for medical imaging of the desired scan area.

In accordance with another aspect of the invention, an open magnet MRI is disclosed having a moveable patient table to move a patient within an open magnet MRI in order to position a desired patient scan area within the FOV of the open magnet MRI. The open magnet MRI has an upper magnetic structure and a lower magnetic structure. The moveable patient table moves fore and aft within a gap formed between the upper and lower magnetic structures. The upper magnetic structure has a first alignment light source mounted on an outer periphery to emit a light beam in longitudinal alignment within a center point of the FOV. A second alignment light source is positioned to emit a second light beam downwardly from the upper magnetic structure to indicate an interior reference point of the FOV.

In accordance with yet another aspect of the invention, a method of accurate patient placement is described for use in an MRI device and includes the steps of placing a patient on a moveable table, positioning the moveable table into the MRI device, and repositioning the patient table within the MRI device based on a beam of light emitting from within the MRI device to denote a location of the FOV without withdrawing the patient.

Various other features, objects and advantages of the present invention will be made apparent from the following detailed description and the drawings.

BRIEF DESCRIPTION OF THE DRAWINGS

The drawings illustrate the best mode presently contemplated for carrying out the invention.

In the drawings:

FIG. 1 is a perspective view of an open magnet MRI incorporating the present invention.

FIG. 2 is a side elevational view of the open magnet MRI of FIG. 1 having a patient placed thereon.

FIG. 3 is a top plan view of FIG. 2 having a portion of the open magnet MRI shown in section.

DETAILED DESCRIPTION OF THE PREFERRED EMBODIMENT

Figure 4:
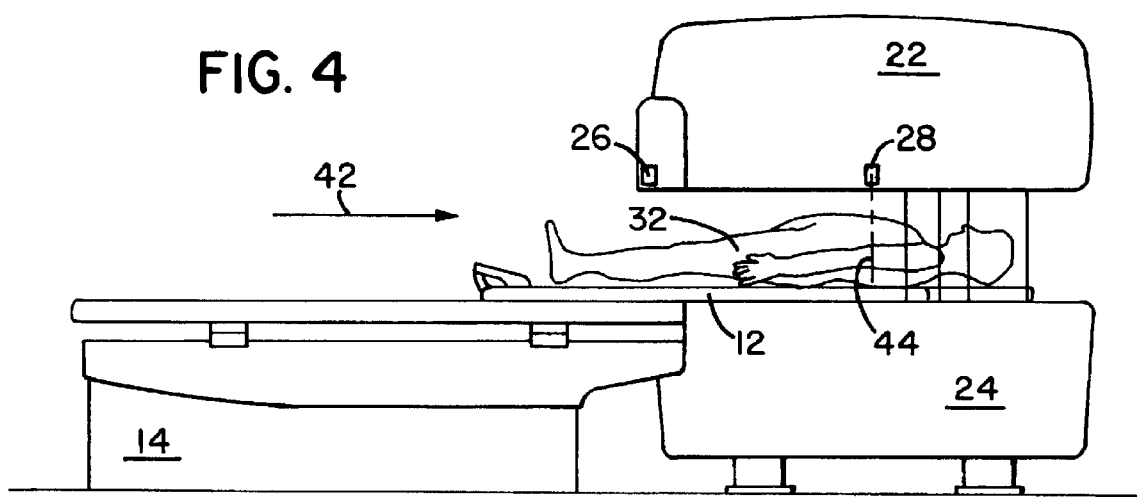
FIG. 4 is a side elevational view similar to FIG. 2, but with a patient positioned within the open magnet MRI.

Open magnet magnetic resonance imaging (MRI) devices use permanent magnets arranged in a manner that provides a maximum amount of open space for patients that cannot, or are apprehensive to, enter a conventional tunnel-type MRI device. One disadvantage of open magnet MRIs is the relatively small region of homogeneity for acquiring quality MRI images. Typically, this provides an imaging area, known as a field-of-view (FOV), of approximately 40 cm. In order to acquire the best image from such a limited FOV, it is desirable to have the center of the FOV directly over the desired scanning area of the patient.

FIG. 1 shows an open magnet MRI 10 having a moveable patient table 12 moveable with respect to a stationary table base 14. The moveable table 12 moves longitudinally from a front end 16 of the table base 14 to a back end 18 of the open magnet MRI 10 by action of a motor (not shown) located in the table base 14 in a manner that is known. The open magnet MRI 10 includes a housing 20 generally, that includes an upper magnetic structure 22 and a lower magnetic structure 24, each of which has therein a magnetic pole face. A pair of lateral supports 23, 25 support the upper magnetic structure 22 over the lower magnetic structure 24. The upper magnetic structure 22 includes a first alignment light 26 on a front, exterior surface 27 of the upper magnetic structure 22. A second alignment light 28 is located on an interior of the upper magnetic structure 22 for repositioning a patient on the moveable patient table 12 when positioned within a gap 30 formed between the upper and lower magnetic structures 22, 24.

The moveable patient table 12 is for aligning a patient 32, as shown in FIG. 2, within an imaging area of the open magnet MRI 10. FIG. 2 shows the patient 32 positioned on the moveable patient table 12 partially within the open magnet MRI 10, such that a desired patient scan area, denoted generally by arrow 34, is centered about a light beam 36 emitted from the exterior alignment light 26.

The first alignment light 26 is used to align the desired scan area 34 of the patient 32 within a fixed reference distance from a center 38, FIG. 3 of the FOV 40. Once the patient is properly positioned using the light beam 36 to center the desired scan area 34, the moveable patient table 12 is automatically incremented longitudinally inward, as indicated by arrow 42 of FIG. 4, a given distance that is equal to the fixed distance between the exterior alignment light 26 and the center 38 of the FOV 40, as best viewed in FIG. 5. Although it may appear that the FOV 40 would generally capture the desired scan area of the patient, since image quality trails off with distance from the center of the FOV 40, the highest quality images are acquired at the center of the FOV. However, an MRI operator can only approximate the exact position of organs, or other structure, of any given patient. Therefore, and in accordance with the present invention, after an initial MRI is acquired, a second alignment light 28 is used to emit a second beam of light 44 from the interior of the upper magnetic structure 22 along the center 38 of the FOV 40 to reposition the patient accordingly.

Figure 5:
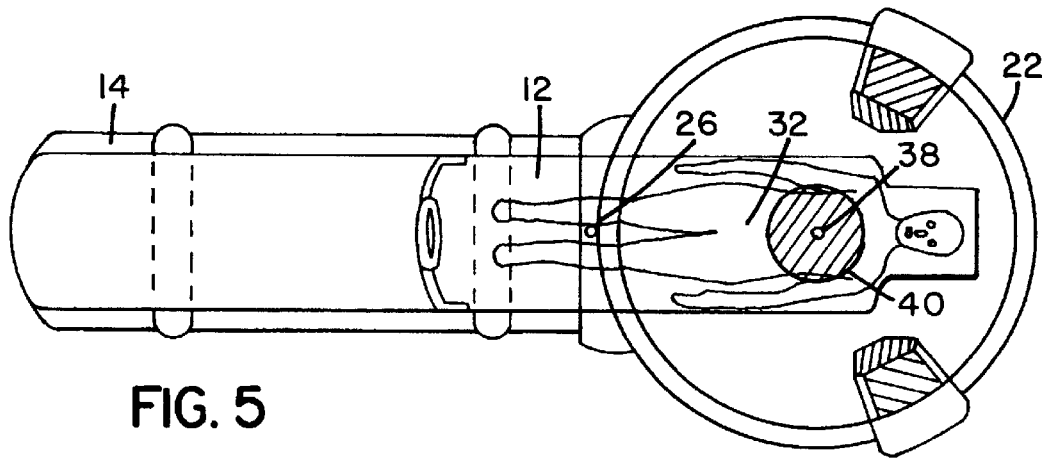
FIG. 5 is a top plan view of FIG. 4 having a portion of the open magnet MRI shown in section, similar to FIG. 3.
Figure 6:
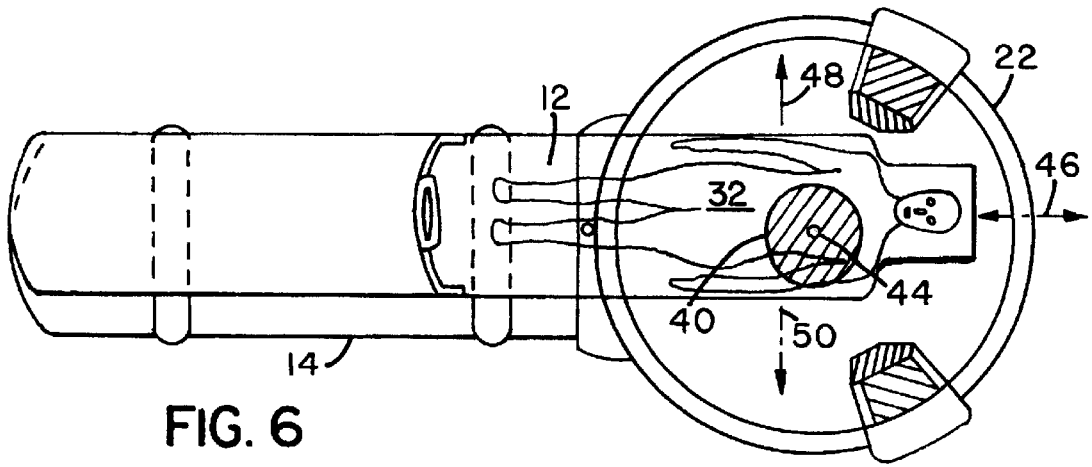
FIG. 6 is a is a top plan view similar to FIG. 5 and showing the repositioning of a patient.

In operation, after a patient is initially positioned by placing the patient so that the estimated scan location is centered about the exterior light beam 36, FIGS. 2–3, then the patient is automatically moved into the open magnet MRI, as in FIGS. 4–5, so that the estimated scan location is now centered within the FOV 40. An initial MRI is then acquired to determine if the patient is properly positioned, and if not, the patient 32 can be adjusted, as shown in FIG. 6, fore and aft in a longitudinal direction 46, or left 48 or right 50 by using the interior light beam 44 as a reference point to indicate the center of the FOV 40. The desired scan area of the patient can then be accurately centered within the FOV without having to move the patient out of the MRI structure.

Figure 7:
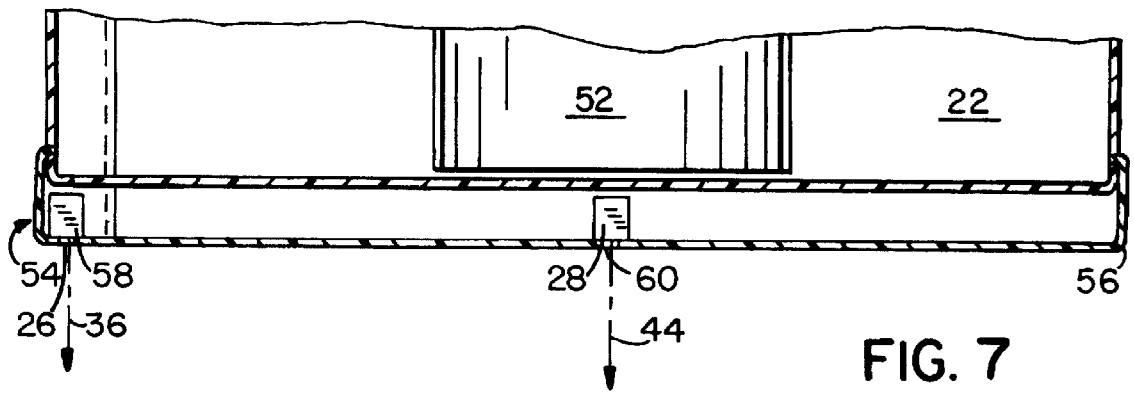
FIG. 7 is a side cross-sectional view of a portion of FIG. 1.

FIG. 7 shows an enlarged, partially cross-sectioned view of the upper magnetic structure 22 having a magnet 52 therein. The first alignment light 26 is shown located on an outer periphery 54 of the upper magnetic structure 22 and within a subhousing 56 having a first opening 58 therein to emit the first light beam 36. The second, interior alignment light 28 is positioned about a center of magnet 52 within the subhousing 56 and above a second opening 60 to emit a second light beam 44 therefrom. It is also contemplated to position the second alignment light 28 above the magnet 52 such that the light beam 44 would emit down a center opening in the magnet 52 and through opening 60.

Figure 8:
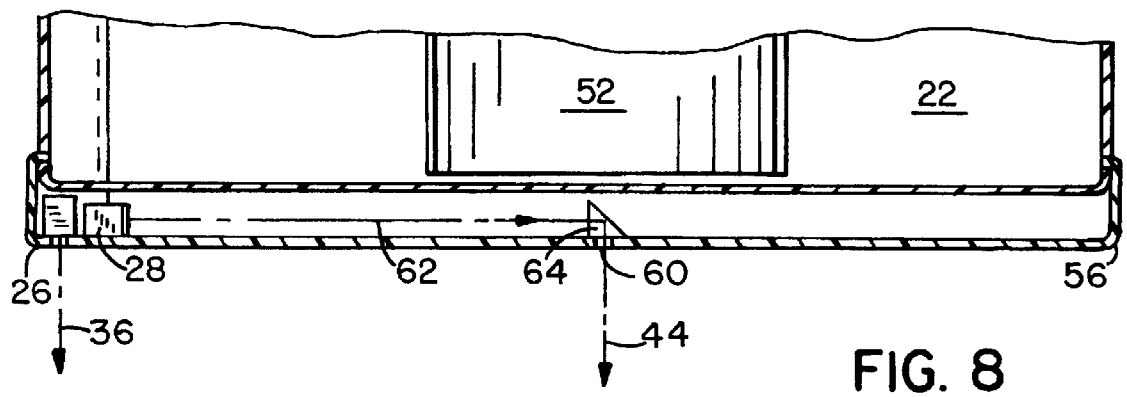
FIG. 8 is a side cross-sectional view of a portion of FIG. 1, similar to FIG. 7, showing an alternate embodiment.

FIG. 8 shows yet another embodiment in which the second alignment light 28 is mounted adjacent the first alignment light 26 and directs light horizontally 62 toward a redirectional device 64 to redirect the horizontal beam of light 62 from the second alignment light 28 downwardly so that light beam 44 passes through opening 60 and toward the patient. The redirecting device 64 can include a light redirecting prism, a non-magnetic mirror, or any other structure to redirect the light beam as necessary.

Accordingly, the invention includes a method of accurate patient placement in an MRI structure that includes placing a patient 32 on the moveable table 12 and providing an exterior alignment light 26 on an outer periphery 54 of the MRI structure 10, a fixed distance from a center 38 of the FOV 40, such that the alignment light 26 is in longitudinal alignment with the center 38 of the FOV 40. The method includes emitting a light beam 36 from the exterior alignment light 26 to transfer the center 38 of the FOV 40 the fixed distance outside the MRI structure to allow an MRI operator to align an estimated scan location of the patient to be within the FOV as accurately as possible. After the moveable table is positioned into the MRI structure, the method includes taking an initial MRI scan to determine whether the estimated patient scan location is sufficiently within the FOV to capture the desired scan area of the patient, and if not, repositioning the patient on the patient table within the MRI structure based on a second beam of light from the second, interior alignment light 28. Such repositioning ensures that the desired scan area of the patient is actually centered within the FOV without having to move the patient out of the MRI structure.

The present invention has been described in terms of the preferred embodiment, and it is recognized that equivalents, alternatives, and modifications, aside from those expressly stated, are possible and within the scope of the appending claims.

What is claimed is:

1. A patient positioning device for use in medical imaging of patients comprising:

a medical imaging housing having upper and lower magnets forming an open magnet MRI and accepting therein a moveable table for placement thereon of a patient; and an interior alignment light positioned within an upper portion of the medical imaging housing to emit an interior light beam from an interior of the upper portion of the housing toward a patient on the moveable table within the housing to align a desired scan area of the patient within a scanning region for medical imaging of the desired scan area.

2. The patient positioning device of claim 1 further comprising:

an open magnet MRI having an upper pole face and a lower pole face, and a lateral structure connecting the upper and lower pole faces, the open magnet MRI creating a field-of-view (FOV) to image a specific region of a patient; and an exterior alignment light located on an outer periphery of the upper pole face and directing a light beam downwardly toward an estimated scan location of the desired scan area of the patient on the moveable table, the light beam in longitudinal alignment with a center of the FOV a given distance away from the center of the FOV.

3. The patient positioning device of claim 2 further comprising a means for repositioning a patient after acquiring an image of the estimated scan location that did not coincide with the desired scan area of the patient.

4. The patient positioning device of claim 2 wherein the interior alignment light is positioned in the upper pole face and the light beam is emitted through a center hole of a magnet within the center of the FOV.

5. The patient positioning device of claim 1 wherein the medical imaging housing has in upper housing and comprises a repositioning device located in the upper housing to redirect the interior light beam from being generally horizontal in the upper housing to being generally perpendicular to the moveable table.

6. The patient positioning device of claim 5 wherein the repositioning device is a non-magnetic reflective surface.

7. The patient positioning device of claim 5 wherein the repositioning device is a prism capable of redirecting light at a 90° angle.

8. The patient positioning device of claim 1 wherein the moveable table is lockable in a fixed position and wherein the interior alignment light emits light when the moveable table is not locked in the fixed position.

9. In an open magnet MRI having a moveable patient table to move a patient within an open magnet MRI to position a desired patient scan area within a field-of-view (FOV) of the open magnet MRI, the open magnet MRI having an upper magnetic structure and a lower magnetic structure, wherein the moveable patient table moves fore and aft within a gap formed between the upper and lower magnetic structures, and wherein the upper magnetic structure has thereon a first alignment light source on an outer periphery to emit a light beam in longitudinal alignment within a center of the FOV, and further comprising:

a second alignment light source positioned in an interior of the upper magnetic structure to emit a second light beam downwardly from the upper magnetic structure to indicate an interior reference point of the FOV.

10. The open magnet MRI of claim 9 wherein the second light source emits a beam of visible light centered within the FOV of the open magnet MRI.

11. The open magnet MRI of claim 9 wherein the second light source is located remotely from the FOV and further comprises a light redirectional device positioned about the upper magnetic structure to redirect a horizontal light beam from the second light source downwardly to a patient and into the FOV.

12. The open magnet MRI of claim 11 wherein the light redirectional device is a non-magnetic mirror.

13. The open magnet MRI of claim 11 wherein the light redirectional device is a light redirecting prism.

14. The open magnet MRI of claim 10 wherein the light beam is emitted downwardly into a center of the FOV in longitudinal alignment with the first alignment light source.

15. The open magnet MRI of claim 9 wherein the second alignment light source is mounted within the upper magnetic structure and emits a beam of light downwardly through a hole in an upper magnet.

16. A method of accurate patient placement in an MRI device comprising the steps of:

placing a patient on a moveable table;

initially aligning the patient with a light outside of an open magnet MRI;

positioning the moveable table into the MRI; and repositioning the patient table to a center position of a FOV within the open magnet MRI based on a beam of light originating from within the open magnet MRI to denote a location of a FOV.

17. The method of claim 16 further comprising the steps of:

providing an exterior alignment light on an outer periphery of the MRI device a given distance from a center of the FOV and in longitudinal alignment within the center of the FOV; and emitting a light beam from the exterior alignment light to transfer the center of the FOV the given distance outside the MRI device.

18. The method of claim 17 further comprising the steps of:

estimating a scan location of a desired scan area of the patient, before the step of positioning the moveable table into the MRI device, moving the patient to place the estimated patient scan location within the light beam from the exterior alignment light; and after the step of positioning the moveable table into the MRI device, taking an initial MRI scan to determine whether the estimated patient scan location is sufficiently within the FOV to capture the desired scan area, and if not, turning on the beam of light within the MRI device, and using the beam of light as a reference point, moving the patient such that the desired scan area of the patient is adequately within the FOV without moving the patient out of the MRI device.

19. The method of claim 16 further comprising the steps of:

locating a light source for the beam of light outside the FOV of the MRI; and redirecting the beam of light within the FOV.

20. The method of claim 19 wherein the step of redirecting the beam of light includes focusing the beam of light to a center of the FOV.

21. A patient positioning device for use in medical imaging of patients comprising:

a medical imaging housing accepting therein a moveable table for placement thereon of a patient; and a single interior alignment light emitting an interior light beam from within a centralized portion of the medical imaging housing towards a patient on the moveable table to align a desired scan area of the patient within a scanning region for medical imaging of the desired scan area, wherein only an intersection of the interior light beam and the moveable table defines a field-of-view (FOV) that has a plane that is parallel to the moveable table.

22. The patient positioning device of claim 21 wherein the FOV is circular.

23. The patient positioning device of claim 22 wherein the interior light beam defines a center of the FOV.

24. A patient positioning device for use in medical imaging of patients comprising:

medical imaging housing having upper and lower magnets forming an open magnet MRI and accepting therein a moveable table for placement thereon of a patient;

an exterior alignment light positioned to emit an exterior light beam about an outer periphery of the medial imaging housing to orient a desired scan area of the patient with respect to a FOV within the open magnet MRI; and an interior alignment light emitting all interior light beam from within the housing toward a patient on the moveable table to align the desired scan area of the patient within the FOV for medical imaging of the desired scan area wherein the interior light beam is substantially perpendicular in direction to the movable table.

* * * * *

UNITED STATES PATENT AND TRADEMARK OFFICE
CERTIFICATE OF CORRECTION

PATENT NO. : 6,294,915 B1
DATED : September 25, 2001
INVENTOR(S) : Murphy, Lawrence et al.

It is certified that error appears in the above-identified patent and that said Letters Patent is hereby corrected as shown below:

Column 3,
Line 40, delete "alter" and substitute therefor -- after --.

Column 5,
Line 6, delete "in" and substitute therefor -- an --.
Line 58, insert -- open magnet -- before "MRI"

Column 6,
Line 51, insert the word -- a -- before "medical"

Signed and Sealed this

Twenty-third Day of April, 2002

Attest:

Attesting Officer

JAMES E. ROGAN
Director of the United States Patent and Trademark Office